United States Patent
Vanevenhoven et al.

(10) Patent No.: US 12,122,986 B2
(45) Date of Patent: Oct. 22, 2024

(54) CRYOGENIC HOP LUPULIN OR CANNABIS TRICHOME PELLETS

(71) Applicant: YAKIMA CHIEF HOPS, INC, Yakima, WA (US)

(72) Inventors: Karl P. Vanevenhoven, Yakima, WA (US); Benjamin T. Grogan, Richland, WA (US); Nicholas S. Zeigler, Yakima, WA (US)

(73) Assignee: Yakima Chief, Inc., Yakima, WA (US)

( * ) Notice: Subject to any disclaimer, the term of this patent is extended or adjusted under 35 U.S.C. 154(b) by 83 days.

(21) Appl. No.: 17/538,711

(22) Filed: Nov. 30, 2021

(65) Prior Publication Data

US 2022/0315870 A1 Oct. 6, 2022

Related U.S. Application Data

(62) Division of application No. 16/129,776, filed on Sep. 12, 2018, now Pat. No. 11,214,765.

(60) Provisional application No. 62/557,678, filed on Sep. 12, 2017.

(51) Int. Cl.
*A61K 36/185* (2006.01)
*C12C 3/06* (2006.01)

(52) U.S. Cl.
CPC .............. *C12C 3/06* (2013.01); *A61K 36/185* (2013.01)

(58) Field of Classification Search
None
See application file for complete search history.

(56) References Cited

FOREIGN PATENT DOCUMENTS

WO      WO-0006691 A1 * 2/2000 ............... B07B 1/22

OTHER PUBLICATIONS

Meyer, YCH Hops Introduces New Cryo Hops TM Product Line, probrewer.com, Feb. 17, 2017, pp. 1-6 vBulletin Solutions, Inc. El Sugundo, US. (Year: 2017).*

* cited by examiner

*Primary Examiner* — Russell G Fiebig
(74) *Attorney, Agent, or Firm* — Svendsen Legal, LLC

(57) ABSTRACT

An enriched trichome pellet product including either a hop derived lupulin component or a cannabis derived trichome component, and the associated cryogenic and mechanical method for the efficient production of the pellet product. The pellet is produced at low temperatures, which aids in pellet production eliminating degradation of the hop lupulin having a high alpha acid and essential oils content that is especially suited for use in the brewing of beer and hop flavored beverages, and aids in eliminating degradation of the cannabis trichome having aromatic oils, and terpenoids and terpenes as well as therapeutic and psychoactive cannabinoids including THC, CBG, and CBD that is especially suited for use in cannabis component or "cannabinoid" enriched products.

9 Claims, 4 Drawing Sheets

CRYOGENIC HOP LUPULIN OR CANNABIS TRICHOME PELLETS

TECHNICAL FIELD

A trichome or hop lupulin-rich pellet product having a concentrated alpha acid and essential oil content, derived from primarily the lupulin component of the hops or the trichome component of cannabis flower buds, and the associated cryogenic and mechanical method for producing an enriched pellet. Lupulin Glands, termed "lupulin," are glandular trichomes found in the hop cone. Similarly, glandular trichomes are found in the female flower, or "bud," of the cannabis plant. More specifically, a high-lupulin or high-trichome content pellet produced in a nitrogen-rich environment with low oxygen content and at low temperatures, with features in production to improve quality and eliminate degradation of the components of interest in lupulin or trichome as compared to conventional processing, the hop lupulin pellet product especially suited for use in the brewing and dry hopping of beer and hop flavored beverages, and the trichome pellet especially suited for use in cannabis component or "cannabinoid" enriched products.

BACKGROUND OF THE INVENTION

The conventional production of 'enriched' or lupulin hop pellets relies on the fact that the bitter resins and essential oils of hops are concentrated in the lupulin glands of the hop cone. Generally, the hop cone includes lupulin glands' (simply referred to as lupulin), 'bract' material (which can be considered to include the hop bracts and bracteoles), and strigs (or connective stems). The lupulin is mechanically separable at sub-freezing temperatures from the bract material and strigs by a sieve or sifter, with the hop cone's lupulin component separation being critical to efficient processing. Lupulin processing is best accomplished without the resinous lupulin glands sticking or clumping within the hop cones, or adhering to and clogging the separation equipment and conveying apparatus. Lupulin powder can be packaged and used in brewing, but converting the powder to a pellet form while maintaining quality is considered preferable and easier to handle on both the production side (less dust) and for the end-user, as pellets dissolve into the beer more readily than powder, which forms a floating raft on the liquid surface. Importantly, the mechanical process of producing enriched hop pellets with the lupulin as a major component of the pellet, relies on an efficient separation of the milled hop cones with the lupulin concentrated included in a fine fraction, and the bracts and strigs concentrated in a coarse fraction, in a separation process.

Botanically, the cannabis plant and the hop plant are closely related. The hop plant is a member of the genus *Humulus*, in the family Cannabinaceae. The family Cannabinaceae also contains marijuana's genus *Cannabis*. Marijuana or cannabis that is grown primarily for fiber, containing low levels of psychoactive and therapeutic compounds is sometimes also referred to as 'hemp.'

Female hop plants have flower cones or "inflorescences," which technically can be referred to as a "strobile," and includes round spikes and papery bracts. The flower, "cola" or "bud" of the cannabis plant is somewhat similar to the hop plant cone, the cannabis plant's inflorescence or "cola" actually refers to a cluster of individual buds or "florets" that grow together tightly. While smaller colas occur along the budding sites of lower branches, a main cola, sometimes called the "apical bud" and forms at the very top of the plant.

A "bract" is a petal-like plant structure that encapsulates the female hop cone, and also included in the female cannabis bud reproductive parts. Additionally in the cannabis bud, a calyx is included, which is a collection of petal-like sepals on the flower or floret. In the case of female cannabis florets, the bracts and calyx appear as small, green tear-shaped leaf-like structures, and are heavily covered in resin glands or "glandular trichomes." For cannabis, the trichomes on the bracts and calyx produce the highest concentration of aromatic oils, terpenoids and terpenes, as well as therapeutic and psychoactive cannabinoids including Tetrahydrocannabinol (THC), Cannabigerol (CBG), and Cannabidiol (CBD).

Similarly, the hop cone is made up of bracts and smaller bracteoles that are attached to a central strig, and the lupulin glands of the hop, which are also "glandular trichomes," contain hop acids and essential oils valued in brewing hop flavored beverages, including terpenes, thiols, thioesters, aliphatic hydrocarbons, oxygenated esters, alcohols, acids, ketones, aldehydes, epoxides, and other more minor components. The blanket of crystalline and resinous trichomes of the on the exterior of a cannabis bud is very similar to the fine yellow lupulin powder trichomes within the hop cone. Powder comprised by Trichomes can be packaged and used in the making of cannabinoid products, but converting the powder to a pellet form offers a preferable product that is easier to measure and handle for the industry and end user.

Several difficulties arise in prior lupulin hop or trichome cannabis pellet production methods, especially with the increasing production of newer, high-alpha hop varieties and hybrid cannabis varieties, which are more resinous and 'sticky,' requiring lower temperature processing and handling methods. However, lower temperature processing of the hop cones or cannabis buds can result in a shattering of the hop cone or flower material, which leads to unwanted particulate material in the fine fraction lupulin or fine fraction trichome product streams. The present invention provides a low temperature or cryogenic separation and pelletizing process that efficiently and reliably produces an enriched hop or cannabis pellet product, high in lupulin containing concentrated alpha acid and essential oil content for hops, and high in aromatic oils and cannabinoids for cannabis.

The following is a disclosure of the present invention that will be understood by reference to the following detailed description taken in conjunction with the accompanying drawings.

Figure 1:
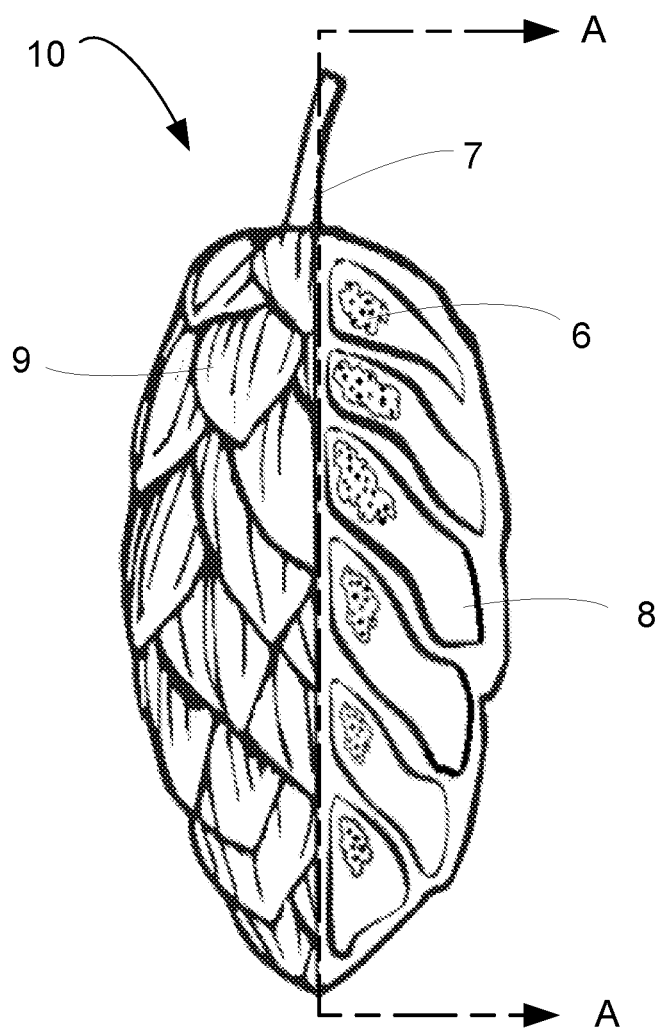
FIG. 1 is a cutaway view of a hop cone detailing component parts of the hop cone as used in a hop lupulin pellet process, according to an embodiment of the invention.

Reference characters included in the above drawings indicate corresponding parts throughout the several views, as discussed herein. The description herein illustrates one or more preferred and alternative embodiments of the invention, and the description herein is not to be construed as limiting the scope of the invention in any manner. It should be understood that the above listed figures are not necessarily to scale and that the embodiments may be illustrated by fragmentary views, graphic symbols, diagrammatic or schematic representations, and section lines. Details that are not necessary for an understanding of the present invention by one skilled in the technology of the invention, or render other details difficult to perceive, may have been omitted.

DETAILED DESCRIPTION OF SPECIFIC EMBODIMENTS

Figure 2:
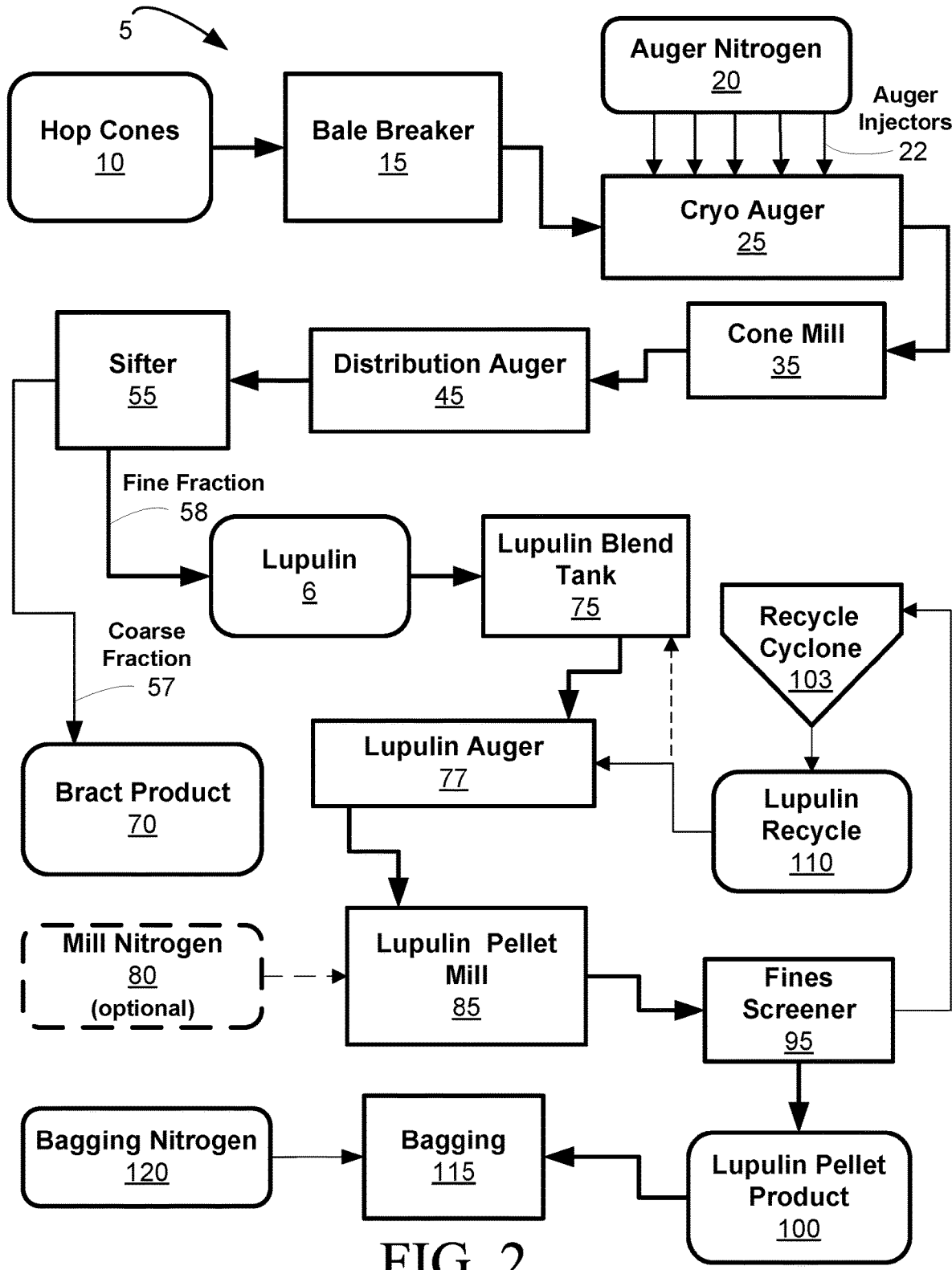
FIG. 2 is a schematic view of a hop lupulin pellet process, according to an embodiment of the invention.

The present invention provides a Lupulin Pellet Process 5, and the products of this novel process, with FIG. 1 showing features of a single Hop Cone 10 and FIG. 2 showing a schematic flow chart of preferred embodiments of the Lupulin Pellet Process, which produces an enriched pellet with concentrated Lupulin 6, having features according the present invention. This concentrated resin pellet contains alpha acid and hop oil, which are components valuable in the brewing process for adding bitterness, flavor and aroma.

Figure 3:
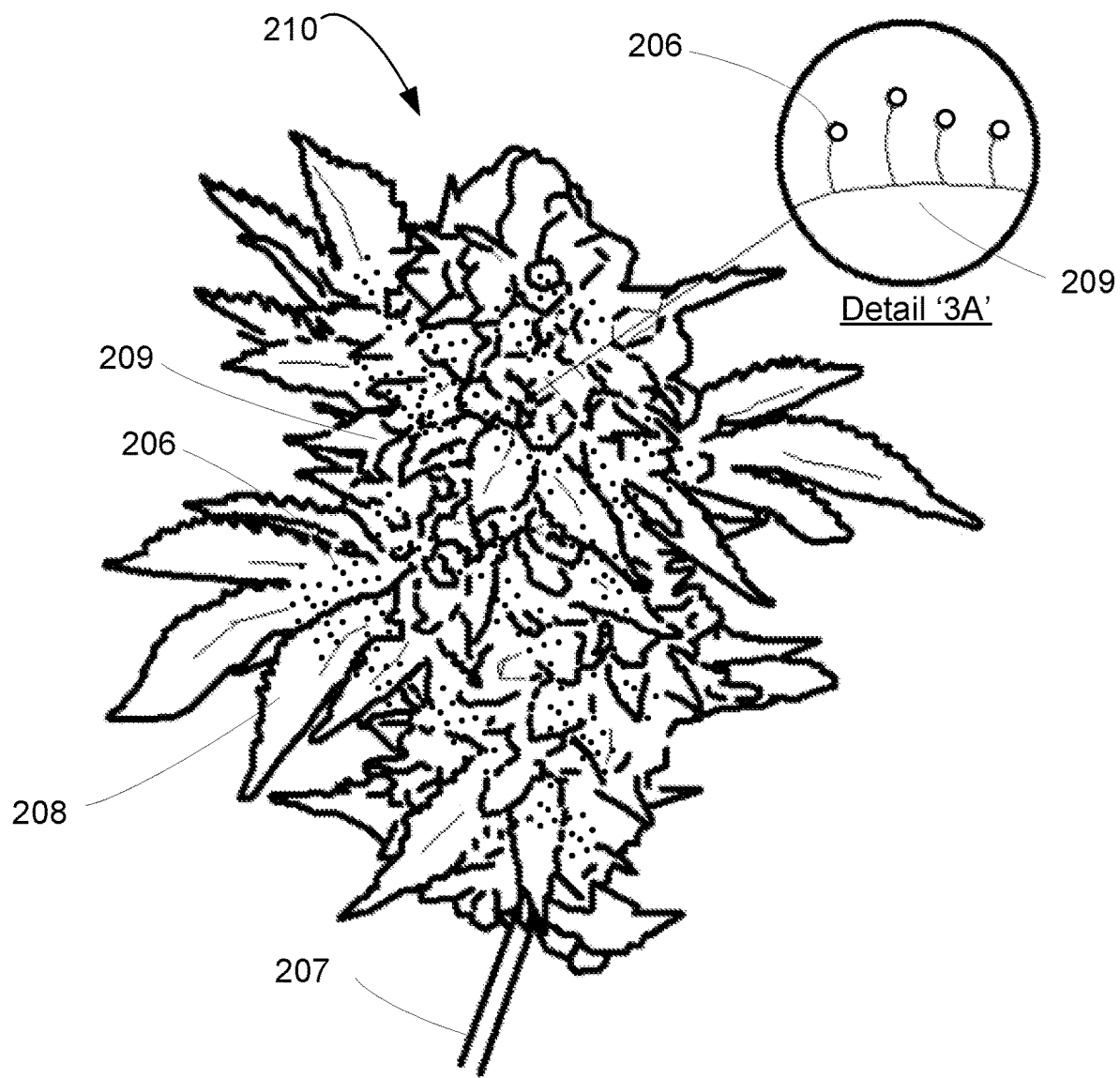
FIG. 3 is a cutaway view of a cannabis bud detailing component parts of the cannabis bud as used in a cannabis trichome pellet process, according to an embodiment of the invention.
Figure 4:
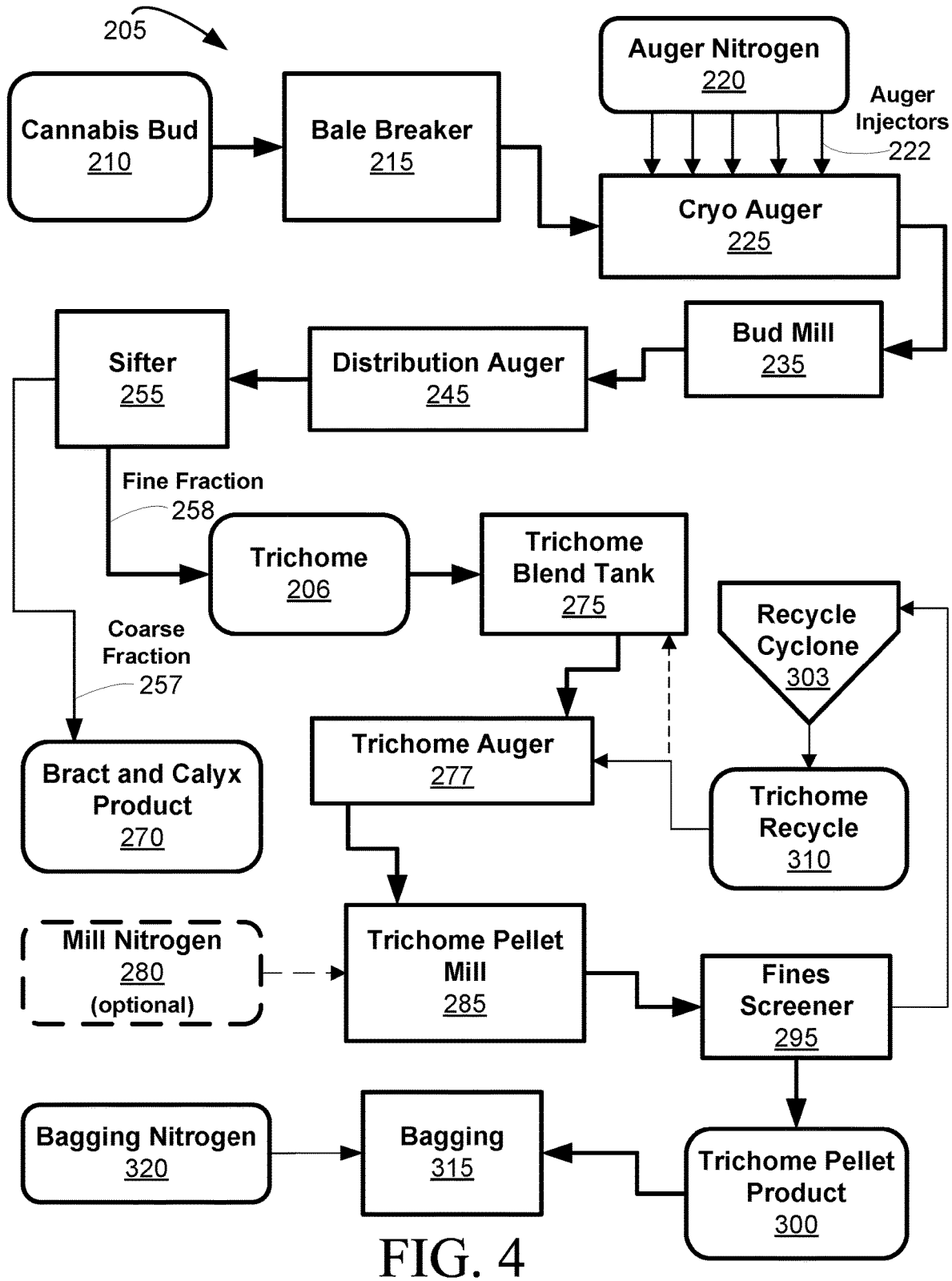
FIG. 4 is a schematic view of a cannabis trichome pellet process, according to an embodiment of the invention.

Alternatively, the present invention provides a Trichome Pellet Process 205 potentially for use with cannabis, and the products of this novel process, with FIG. 3 showing features of a single Cannabis Bud 210 and FIG. 4 showing a schematic flow chart of predicted, preferred embodiments of the Trichome Pellet Process, which produces an enriched or 'high cannabinoid' pellet primarily comprised by Trichomes 206 as well as a pellet with carefully modulated contents of bract and calyx material for flavor also having features according the present invention.

Hop Lupulin Pellet Process:

The single Hop Cone 10 diagramed in FIG. 1 is quarter-sectioned along line A-A to reveal the component structure within. The Hop Cone includes a strig 7 that attaches the Hop Cone to a hop bine, a bract 9 that is the leafy outer petal of the Hop Cone, and a bracteole 8 that is the internal leafy petal material of the Hope Cone, which is where the Lupulin Gland 6 is contained within the Hop Cone. The Lupulin is the resin filled glandular trichome of the Hop Cone that contain the aromatic compounds and essential oils most desired for beer and beverage flavoring.

In contrast to existing approaches, the Lupulin Pellet Process 5 will make use of a liquid Nitrogen ($N_2$), liquid Argon (Ar) or liquid Carbon Dioxide ($CO_2$) to separate the Hop Cone 10 into constituent elements, separate these components from each other, and compress the Lupulin into a user-friendly Lupulin Pellet Product 100. Alternatively, any cryogenic liquid could be used in the Lupulin Pellet Process instead of the liquid $N_2$, including any liquefied and inert gas that can provide a cooling effect when flashed to atmospheric conditions, such as a liquid CO2, or a liquid argon, among others if desired.

The Lupulin Pellet Process 5 is shown schematically in FIG. 2, with Hop Cones 10 fed into a Bale Breaker 15, where the Hop Cones are gently separated from each other and able to flow into a Cryo Auger 25. Typically, the Hop Cones are stored in bales, most preferably with the bales at a bulk density of approximately 10 lb/ft 3 to 14 lb/ft 3 (160 kg/m3 to 224 kg/m3). Preferably, a 'low-impact' type of Bale Breaker is used. The lower density baling and low impact handling in the Bale Breaker is desirable in order to avoid damage or rupture to the Lupulin 6, which is in the form of tiny resinous particles, often referred to as "glands."

Also notably, the terms "approximately" or "approximate" are employed herein throughout, including this detailed description and the attached claims, with the understanding that the terms denote a level of exactitude commensurate with the skill and precision common within the particular field of endeavor, as applicable.

Again, the Lupulin 6 must not be crushed within the stored bales, and preferably baled and stored in a refrigerated warehouse, especially if there is any delay after the harvesting, stripping or picking, and baling of the Hop Cones. Preferably, the processing environment for the Lupulin Pellet Process 5 is refrigerated and kept cool below 50 degrees F. (10.0 degrees C.). Most preferably, the Cryo Auger 25 that receives the Hop Cones 10 from the Bale Breaker 15 is a specially adapted or retrofitted horizontal or inclined auger, having a multiple of Auger Injectors 22 for injecting Auger Nitrogen 20 into the Cryo Auger.

The Auger Nitrogen 20 is most preferably a liquid nitrogen that is sprayed through the system of Auger Injectors integrated into the Cryo Auger 25. Again, instead of the liquid $N_2$ the Auger Nitrogen can be substituted by any cryogenic liquid, which is preferably a liquefied and inert gas that can provide a cooling effect when flashed to atmospheric conditions, such as a liquid CO2, or a liquid argon, among others, if desired. The Auger Injectors 22 are preferably positioned at regular spacings along its auger screw. The Auger Injectors' nozzles are selected to spray liquid nitrogen onto the Hops Cones, where the Auger Nitrogen flashes and super-cools the Hop Cones as the cryogenic fluid flashes to gas to achieve efficient cooling as is well known to those skilled in cryogenic cooling apparatus. Preferably, regularly spaced nozzles are employed along both sides of the length of the Cryo Auger, each with a metered feed rate of 0.05 gallons of liquid $N_2$ to 0.25 gallons of liquid $N_2$, per pound of Hop Cones 10, to best achieve a target temperature of approximately −50 degrees F. to 10 degrees F. (−45.6 degrees C. to −12.2 degrees C.) for the Hop Cones feeding from the Cryo Auger into the Cone Mill 35. Alternatively, the Auger Injector may simply be holes or penetrations through the inside wall of the Cryo Auger, the holes sized and shaped to function as spray nozzles for the Auger Nitrogen.

The quality of the Lupulin Pellet Product 100 that eventually results from processing the Hop Cones 10 with the Cone Mill 35 and then the Sifter 55 is greatly improved when the Lupulin 6 is frozen, granular and non-sticky, as occurs when the Hop Cones are precooled to render the resinous oil portions of the hop substantially solid. The Hop Cones cooled in the Cryo Auger 25 feed into the Cone Mill, as shown in FIG. 2.

The Cone Mill 35 is preferably a standard industrial mill, as typical of the Fitzpatrick™ brand of milling machines. The Cone Mill is preferably of stainless steel, food grade construction, controlled by a variable speed drive, as is selectable by those skilled in hop milling and processing. The Cone Mill functions to gently separate the bracts from the strig, thereby exposing the Lupulin Glands of the in-fed Hop Cones 10 into component pieces, preferably running at a slow-speed setting to maintain the Lupulin 6 substantially intact. The Cone Mill serves to fracture and separate the component parts of the Hop Cones without overly crushing, grinding them into fines, or compressing them together.

A Distribution Auger 45 delivers the gently milled and fragmented, and super-cooled Hop Cones 10 from the Cone Mill 35 to a Sifter 55, as shown in FIG. 2. The Sifter performs a sieving or sifting process, preferably with a vibrating rotary drum sifter as typical of BUHLER™ brand of rotary sifters. The rotating drum sifter is well suited for the scraping removal of oversize product from the drum sifter's screen. In addition, rotating drum sifters provide tremendous production capacities with internal beater-bars to move the fine material through a stationary screen along the machine's axis producing a Fine Fraction 58, and to then dispense the oversize product as a Coarse Fraction 57 out an end-chute of the Sifter.

As shown in FIG. 2, the Sifter 55 produces the Coarse Fraction 57 and the Fine Fraction 58. The Fine Fraction produced in the sieving process within the Sifter contains most of the Lupulin 6 in the originally processed Hop Cones 10, and a small portion of the bracts 9, bracteoles 8, and a minute portion of strigs 7. For the present disclosure, the strigs, bracts and bracteoles are together referred to simply as "bracts", or Coarse Fraction, from the Sifter and designated as a Bract Product 70. Even without a significant Lupulin component, the Bract Product contributes pleasant bitterness to flavored beverages, with the unique aroma of higher-resin hop varieties. The Bract Product 70 is also a polyphenol-rich fraction that has beneficial contributions when used in the brewing process as well as in the nutraceutical and pharmaceutical industries.

Processed within the Sifter 55, the glandular particles of the Lupulin 6 in the Fine Fraction 58 only have an approximate diameter between 0.15 mm to 0.20 mm, so the mesh size of the sieve screen in the Sifter can typically range from approximately 0.15 mm to 1.0.

Preferably, after removal of the Coarse Fraction 57 in the Sifter 55, the remaining Fine Fraction 58, which is the Lupulin 6, is fed into a Lupulin Blend Tank 75 as shown in FIG. 2. The Lupulin Blend Tank is used to homogenize, blend and meter and the Lupulin fed into a Lupulin Pellet Mill 85.

The Lupulin Pellet Mill 85 produces standard sized pellets, typically with an approximate preferred diameter die of 0.25 inch, and an overall length of approximately 0.25 inches to 0.75 inches or more, the pellet length and diameter depending on the die selection and in the operator's settings of the Lupulin Pellet Mill. A significant benefit is realized by achieving a high quality Lupulin Pellet Product 100 with the Lupulin Pellet Process 5 of the present invention. Along with increasing adhesion within each pellet of the Lupulin Pellet Product, the Lupulin Pellet Product stays cold and in an atmosphere that is very low in oxygen, preferably less than 2% $O_2$ by volume, with the temperature of the Lupulin 6 entering the Lupulin Pellet Mill between 0 degrees F. and −50 degrees F. (−17.8 degrees C. to −45.6 degrees C.), and most preferably below −20 degrees F. (−28.9 degrees C.).

To provide cooling in the Lupulin Pellet Mill 85, as a counter measure to the heat generated in the die compression process, a Mill Nitrogen 80 can be injected into the die of the Lupulin Pellet Mill, as shown schematically in FIG. 2. Preferably, the Mill Nitrogen is used in a similar fashion to the Auger Nitrogen 20, discussed above. The Mill Nitrogen is also most preferably liquid nitrogen sprayed into the mill to maintain a cold environment in processing and onto the pellets exiting the pellet die where the liquid nitrogen flashes into super-cooled nitrogen gas, absorbing heat energy from the system by virtue of this expansion. Spray nozzles mounted within the Lupulin Pellet Mill are selected to achieve efficient cooling with liquid nitrogen as is well known to those skilled in cryogenic cooling apparatus. The liquid nitrogen process is designed to achieve optimal quality by cold pelleting. Most preferably, the cold pelleting process of the present invention maintains temperature of the Lupulin Pellet Product 100 exiting the Lupulin Pellet Mill at below a temperature of 75 degrees F. (23.9 degrees C.). Due to the cold temperature of the Lupulin 6 entering the Lupulin Pellet Mill 85, Mill Nitrogen 80 is not an industry standard feature employed in pelletization to ensure pellet temperature does not exceed 75 degrees F. (23.9 degrees C.).

From the Lupulin Pellet Mill 85, the Lupulin 6 in predominantly a pellet form is routed to a Fines Screener 95, as shown on FIG. 2. Preferably, the Fines Screener is similar to a SWECO® brand of a round vibratory screener, selected to process the pelleted Lupulin stream from the Lupulin Pellet Mill, with the oversized fraction comprising the Lupulin Pellet Product 100, and the fines or 'unders' from the Fines Screener comprising a Lupulin Recycle 110, which is primarily Lupulin that failed to form a pellet or was shed as the Lupulin Pellet Product exited from the Lupulin Pellet Mill.

In contrast to the Lupulin Pellet Process 5, for a typical enriched lupulin hop pellet processing the rejected oversized fraction from the sieve is routinely sent through the conventional sieve processing step several times, in order to increase lupulin yield by stepwise repeated removal of the unwanted coarse materials. However, a significant improvement in the Lupulin Pellet Process is realized by a single pass processing of the Lupulin 6 though the Lupulin Pellet Mill 85, supplemented with the novel use of the Lupulin Recycle 110, as shown in FIG. 2. This minimalistic processing approach provides a more pure and better quality Lupulin Fraction while simultaneously producing a value added Bract Product 70 with ideal ratios of resin and polyphenols for brewing, which allows a brewer to have a finer control over flavor and aroma development in their brewing process.

Also in contrast to the Lupulin Pellet Process 5, in typical hop pellet processing the pellet product warms to room temperature, often over 70 degrees F. (21.1 degrees C.) in an oxygen-rich environment prior to pelleting. Pelleting at these warm inlet temperature in the presence of oxygen results in excessive heat in the pelleting process commonly over 120 degrees F. (48.9 degrees C.), which often results in a heat damaged and oxidized pellet product, significantly degrading quality. The current invention provides benefits of cooling and processing in a nitrogen environment to preserve alpha acids and delicate essential hop oils. The novel cold processing and Lupulin Recycle 110 additionally provides improved control in pelleting the Lupulin 6 at cold temperatures, further protecting the alpha acids, essential hop oils, and the bract fraction from oxidative and thermal degradation.

The Lupulin Recycle 110 step may utilize the Lupulin Blend Tank 75, which is a conventional type of mixing tank for blending the incoming feed stream of Lupulin 6, as discussed above. Preferably, as shown in FIG. 2, the Lupulin Recycle is first returned to a Recycle Cyclone 103, where the Lupulin Recycle is discharged and returned to a Lupulin Auger 77 that transfers the Lupulin 6 from the Lupulin Blend Tank to the Lupulin Pellet Mill 85.

Alternatively, the Lupulin Recycle 110 from the Recycle Cyclone 103 can be mixed in the Lupulin Blend Tank with the primary component of the Fine Fraction 58 produced by the Sifter 55. Of note, the Lupulin Recycle consists primarily of Lupulin 6 from the Fines Screener 95, processing the outfeed from the Lupulin Pellet Mill 85.

The Lupulin Recycle 110 provides a self-regulating return flow of Lupulin 6 to the Lupulin Pellet Process 5. Specifically, as shown in FIG. 2, the Lupulin Recycle recovers un-pelleted fines from the Fines Screener 95, and feeds into the Lupulin Blend Tank 75, where it is blended with the Lupulin exiting the Sifter 55 as the Fine Fraction 58 of the processed Hop Cones 10. The Recycle Lupulin is primarily Lupulin that initially fails to pelletize in the Lupulin Pellet Mill 85. Lupulin that is too cold to adhere together or compact into pellet form remains as fine particulate, and can be recovered in the Fines Screener 95 and recycled. Importantly, the Lupulin Recycle material warms as it transfers through the process from the Lupulin Pellet Mill and the Fines Screener, and serves to change the physical characteristics of the Lupulin, making it much more suitable for pelleting in the Lupulin Pellet Mill. The Lupulin Recycle, being warmed from sub-zero temperatures to 0 degrees F. up to 65 degrees F. (−17.8 degrees C. up to 18.3 degrees C.), by the pelletizing and screening processes is more tacky and sticky than the incoming Lupulin from the Sifter 55, and will serve to increase cohesion as a sticking agent, when blended with the infeeding Lupulin within the Lupulin blend tank or Lupulin Auger. The cool Lupulin Recycle has proven to be vital to pelleting the super cooled Lupulin within the Lupulin Pellet Mill.

Additionally, the Lupulin Recycle 110 is a self-regulating feedstream, in that the colder the initial Lupulin 6, fed into and processed by the Lupulin Pellet Mill 85, the more Lupulin remains un-pelleted, to pass through the Fines Screener and return to the Lupulin Blend Tank 75, or returned to the Lupulin Auger, in the Lupulin Recycle stream, as discussed above. The Lupulin Recycle in-turn, warms the stream of Lupulin fed into the Lupulin Pellet Mill as the Fine Fraction 58, thereby reducing the amount of un-pelleted Lupulin passing through the Fines Screener, and so reduces the amount of Lupulin Recycle.

As a significant benefit, the Lupulin Recycle 110 serves to maintain product consistency, reduces process waste and because the Lupulin Recycle automatically optimizes the temperature of the Lupulin 6 feeding into the Lupulin Pellet Mill 85, the Lupulin Pellet Process 5 requires less oversight, less monitoring and reduces the need for fine control by process operators. An overall benefit of the Lupulin Pellet Process is that the novel Lupulin Pellet Product 100 of the Lupulin Pellet Process exhibits a significantly higher concentration of alpha acids (currently up to 30%) and oils (currently up to 6.6%) than has been possible with any other prior methods of pelleting.

For the Lupulin Pellet Product 100, the filling and packaging steps or processes are similar to the corresponding steps in the production of standard hop pellets, as is known to persons skilled in the technology of hop pellet processing. An automated apparatus for Bagging 115 is preferably employed as shown schematically in FIG. 2. Additionally, a Bagging Nitrogen 120 is injected into the packaged product, providing an inert atmosphere that is ideal for long term storage, displacing oxygen from the storage bag containing the Lupulin Pellet Product.

Brewing trials with the Lupulin Pellet Product 100 found that the pellets produced by the Lupulin Pellet Process 5 noticeably enhanced hop aroma and flavor contributions to the brewed beverage, specifically citing 'juicy' and 'resinous' characteristics. Also, an average of a two percent to a ten percent increase in brewery yields were reported with the use of Lupulin Pellet Product as compared to conventional hop pellets, primarily due to reduced brewhouse and cellar 'trub,' which is the waste layer of sediment, typically left at the bottom of the hot-side brewing vessels after kettle boil, whirlpool, or in the vessels used for fermentation, dry hopping, and maturation processes.

Cannabis Trichome Pellet Process:

A single Cannabis Bud 210 or "inflorescence" is diagramed in FIG. 3. The Cannabis Bud attaches to a Cannabis Stem 207, and includes a bract 208 that is the leafy outer petal of the Cannabis Bud, and a Calyx 209 that is the internal leafy petal material of the Cannabis Bud, which is where the glandular trichomes are contained within the Cannabis Bud. As shown in Detail '3A' in FIG. 3, the Trichome 206 is the resin filled gland of the Cannabis Bud containing the highest concentrations of desirable aromatic oils and cannabinoids, including THC and CBD.

Traditionally, Trichome 206 separation from the Cannabis Bud 210 is accomplished with an ice water bath and agitator, which fractures the Trichomes, releasing them from the leaf matter which is separated out using a series of static mesh screens that decrease in mesh size. The leaf matter is discarded and the Trichomes retained. Other existing methods for separating Trichomes from Cannabis Bud, and specifically the cannabis bract, petiole and calyxes, include the dry sieving of ground cannabis material, or mechanically rubbing cannabis buds over a series of screens that employ sequentially reducing mesh sizes. In both cases, the plant material is discarded and the high potency Trichomes are either kept as powder or manually pressed into bars of 'hash' from which pieces are broken off and consumed which results in non-standardized and highly variable dosing.

It is observed to be a novel improvement to pelletize Trichome 206, as enabled and described in the Trichome Pellet Process 205 herein, which is an industrial cryogenic and oxygen-depleted method that results in the production of a Trichome enriched Trichome Pellet Product 300. In contrast to existing approaches, the Trichome Pellet Process 205 will make use of liquid nitrogen, as accomplished in the Lupulin Pellet Process 5 as disclosed herein, to separate the Cannabis Buds 210 into constituent elements of trichomes and bract fraction, separate these from each other, and compress the Trichomes into a user-friendly Trichome Pellet Product.

Alternatively, any cryogenic liquid could be used in the Trichome Pellet Process 205 instead of the liquid nitrogen, including any liquefied and inert gas that can provide a cooling effect when flashed to atmospheric conditions, such as a liquid CO2, or a liquid argon, among others among others, if desired.

The Trichome Pellet Process 205 is shown schematically in FIG. 4, with Cannabis Buds 210 fed into a Bale Breaker 215, where the Cannabis Buds are gently separated from each other and able to flow into a Cryo Auger 225. Whether received as loose buds or compressed bales, the Cannabis Buds can be introduced into the process through the Bale Breaker. Preferably, a 'low-impact' type of Bale Breaker is used, with the lower density baling and low impact handling in the Bale Breaker desirable in order to avoid damage or rupture to the Trichome 206, which is in the form of tiny resinous particles, often referred to as "glands."

Again notably, the terms "approximately" or "approximate" are employed herein throughout, including this detailed description and the attached claims, with the understanding that the terms denote a level of exactitude commensurate with the skill and precision common within the particular field of endeavor, as applicable.

Importantly, preferably, the Trichomes 206 on the Cannabis Buds 210 not be crushed within the stored bales, and preferably baled and stored in a refrigerated warehouse, especially if there is any delay after the harvesting, stripping and baling of the Cannabis Buds. Preferably, the processing environment for the Trichome Pellet Process 205 is refrigerated and kept cool below 50 degrees F. (10.0 degrees C.). Most preferably, the Cryo Auger 225 that receives the Cannabis Buds 210 from the Bale Breaker 215 is a specially adapted or retrofitted horizontal or inclined auger, having a multiple of Auger Injectors 222 for injecting Auger Nitrogen 220 into the Cryo Auger.

The Auger Nitrogen 220 is most preferably a liquid nitrogen that is sprayed through the system of Auger Injectors integrated into the Cryo Auger 225. Alternatively, instead of the liquid $N_2$ the Auger Nitrogen can be substituted by any cryogenic liquid, including any liquefied and inert gas that can provide a cooling effect when flashed to atmospheric conditions, such as a liquid $CO_2$, among others if desired. The Auger Injectors 222 are preferably positioned at a regular spacing along its auger screw. The Auger Injectors' nozzles are selected to spray liquid nitrogen onto the Cannabis Buds 210 where the Auger Nitrogen flashes and super-cools the Cannabis Buds as the cryogenic fluid flashes to gas to achieve efficient cooling as is well known to those skilled in cryogenic cooling apparatus. Preferably, regularly spaced nozzles are employed along both sides of the length of the Cryo Auger, each with a metered feed rate of 0.05 gallons of liquid $N_2$ to 0.25 gallons of liquid $N_2$, per pound of Cannabis Buds, to best achieve a target temperature of approximately −50 degrees F. to 10 degrees F. (−45.6 degrees C. to −12.2 degrees C.) for the Cannabis Buds feeding from the Cryo Auger into the Bud Mill 235. Alternatively, the Auger Injector may simply be holes or penetrations through the inside wall of the Cryo Auger, the holes sized and shaped to function as spray nozzles for the Auger Nitrogen The Auger Nitrogen 220 is most preferably a liquid nitrogen that is sprayed through the system of Auger Injectors integrated into the Cryo Auger 225. Alternatively, instead of the liquid $N_2$ the Auger Nitrogen can be substituted by any cryogenic liquid, including any liquefied and inert gas that can provide a cooling effect when flashed to atmospheric conditions, such as a liquid CO2, or a liquid argon, among others, if desired.

The Auger Injectors 222 are preferably positioned at a regular spacing along its auger screw. The Auger Injectors' nozzles are selected to spray liquid nitrogen onto the Cannabis Buds 210 where the Auger Nitrogen flashes and freezes the Cannabis Buds as the cryogenic fluid flashes to gas to achieve efficient cooling as is well known to those skilled in cryogenic cooling apparatus. Preferably, regularly spaced nozzles are employed along both sides of the length of the Cryo Auger, each with a metered feed rate of 0.05 gallons of liquid $N_2$ to 0.25 gallons of liquid $N_2$, per pound of Cannabis Buds, to best achieve a target temperature of approximately −50 degrees F. to 10 degrees F. (−45.6 degrees C. to −12.2 degrees C.) for the Cannabis Buds feeding from the Cryo Auger into the Bud Mill 235. Alternatively, the Auger Injector may simply be holes or penetrations through the inside wall of the Cryo Auger, the holes sized and shaped to function as spray nozzles for the Auger Nitrogen.

The expected Trichome Pellet Product 300 resulting from processing the Cannabis Buds 210 with the Bud Mill 235 and then the Sifter 255 will be greatly improved when the Trichome 206 component of the fine fraction is frozen, granular and non-sticky, as occurs when the Cannabis Buds are precooled to render the resinous oil portions of the cannabis substantially more solid and less tacky. The Cannabis Buds cooled in the Cryo Auger 225 feed into the Bud Mill, as shown in FIG. 4.

The Bud Mill 235 is preferably a standard industrial mill, as typical of the Fitzpatrick™ brand of milling machines. The Bud Mill is preferably of stainless steel, food grade construction, controlled by a variable speed drive, as is selectable by those skilled in hop milling and processing. The Bud Mill functions to gently separate the bract 208 and calyx 209 from the stem 207, thereby gently separating the trichome glands from the in-fed Cannabis Buds 210 into constituent pieces, and preferably running at a slow-speed setting to maintain the Trichome 206 substantially intact. Again, the Bud Mill serves to gently separate the constituent parts of the Cannabis Buds without overly crushing, grinding them into fines, or compressing them together.

A Distribution Auger 245 will deliver the crushed and super-cooled Cannabis Buds 210 from the Bud Mill 35 to a Sifter 255, as shown in FIG. 4. The Sifter performs a sieving or sifting process, preferably with a vibrating rotary drum sifter as typical of BUHLER™ brand of rotary sifters. The rotating drum sifter is well suited for the scraping removal of oversize product from the drum sifter's screen. In addition, rotating drum sifters provide tremendous production capacities with internal beater-bars to move the fine material through a stationary screen along the machine's axis producing a Fine Fraction 258, and to then dispense the oversize product as a Coarse Fraction 257 out an end-chute of the Sifter.

As shown in FIG. 4, the Sifter 255 produces the Coarse Fraction 257 and the Fine Fraction 258. The Fine Fraction produced in the sieving process within the Sifter contains most of the Trichome 206 in the originally processed Cannabis Buds 210, and a small portion of the Bracts 209, Bracteoles 208 and an insignificant portion of the Stems 207. The Fine Fraction 257 is primarily the Trichome of the Cannabis Bud. For the present disclosure, the stems, bracts and calyx are included in the Coarse Fraction from the Sifter and designated as a Bract and Calyx Product 270. Even without a significant Trichome component, the Bract and Calyx Product is a polyphenol-rich fraction that has desirable contributions when used in the certain hemp and cannabis products for the pharmaceutical and cosmetics industries.

Processed within the Sifter 255, the glandular particles of the Trichomes 206 in the Fine Fraction 258 only have an approximate diameter between 0.04 mm to 0.12 mm, so the mesh size of the sieve screen in the Sifter can typically range from approximately 0.07 mm to 0.14 mm, and may be increased up to 1.0 mm for the Trichome Pellet Product 300, which would include a larger portion of the coarser fraction components, that are normally included in the Bract and Calyx Product 270. With the smaller, most preferred mesh sizing in the Sifter, as listed above, a pure Trichome Pellet Product would be produced. However, employing the larger mesh size would provide a uniquely selectable concentration of bract and calyx material along with Trichome 206 in the Fine Fraction 258, and thereby designed to selectably and carefully balance the flavors that reside in the Trichomes as well as the remaining Cannabis Bud 210 material.

Preferably, after removal of the Coarse Fraction 257 in the Sifter 255, the remaining Fine Fraction 258, which is the Trichome 206, is fed into a Trichome Blend Tank 275 as shown in FIG. 4. The Trichome Blend Tank is used to homogenize, blend and meter and the Trichome fed into a Trichome Pellet Mill 285.

The Trichome Pellet Mill 285 produces standard sized pellets, typically with an approximate preferred diameter die of 0.25 inch, and an overall length of approximately 0.25 inches to 0.75 inches or more, the pellet length and diameter depending on the die selection and in the operators settings of the Trichome Pellet Mill, and the breakup of the produced pellets in handling, along with the amount of adhesion present within the pellet.

To provide cooling in the Trichome Pellet Mill 285, as a counter measure to the heat generated in the compression of the die process, Mill Nitrogen 280 can be injected into the die of the Trichome Pellet Mill, as shown schematically in FIG. 4. Preferably, the Mill Nitrogen is used in a similar fashion to the Auger Nitrogen 220, discussed above. The Mill Nitrogen is also most preferably liquid nitrogen sprayed into the mill to maintain a cold environment in processing and onto the pellets exiting the pellet die where the liquid nitrogen flashes into super-cooled nitrogen gas, absorbing heat energy from the system by virtue of this expansion. Spray nozzles mounted within the Trichome Pellet Mill are selected to achieve efficient cooling with liquid nitrogen as is well known to those skilled in cryogenic cooling apparatus.

From the Trichome Pellet Mill 285, the Trichome 206 in predominantly a pellet form is routed to a Fines Screener 295, as shown on FIG. 4. Preferably, the Fines Screener is similar to a SWECO® brand of a round vibratory screener, selected to process a Trichome Pellet Stream 296 from the Trichome Pellet Mill, with the oversized fraction comprising the Trichome Pellet Product 300, and the fines or 'unders' from the Fines Screener comprising a Trichome Recycle 310, which is primarily Trichome that failed to form a pellet.

A significant efficiency in the Trichome Pellet Process is realized by a single pass processing and separation of the Trichome 206 from the Bract and Calyx through the Sifter 255 and the diversion of the Trichomes though the Trichome Pellet Mill 285, supplemented with the novel use of the Trichome Recycle 310, as shown in FIG. 4. This minimalistic processing approach provides a more pure and better quality Trichome Fraction while simultaneously producing and value added Bract and Calyx Product 270

The Trichome Recycle 310 step may utilize the Trichome Blend Tank 275, which is a conventional type of mixing tank for blending the incoming feed stream of Trichome 206, as discussed above. Preferably, as shown in FIG. 4, the Trichome Recycle is first returned to a Recycle Cyclone 303, where the Trichome Recycle is discharged and returned to a Trichome Auger 277 that transfers the Trichome from the Trichome Blend Tank to the Trichome Pellet Mill 285.

Alternatively, the Trichome Recycle 310 from the Recycle Cyclone 303 can be mixed in the Trichome Blend Tank with the primary component of the Fine Fraction 258 produced by the Sifter 255. Of note, the Trichome Recycle consists primarily of Trichome 206 from the Fines Screener 295, processing the outfeed from the Trichome Pellet Mill 285.

The Trichome Recycle 310 provides a self-regulating return flow of Trichome 206 to the Trichome Pellet Process 205. Specifically, as shown in FIG. 4, the Trichome Recycle recovers un-pelleted fines from the Fines Screener 295, and feeds into the Trichome Blend Tank 275, where it is blended with the Trichome exiting the Sifter 255 as the Fine Fraction 258 of the processed Cannabis Bud 210. The Recycle Trichome is primarily Trichome that initially fails to pelletize in the Trichome Pellet Mill 255. Trichome material that is too cold to adhere together or compact into pellet form remains as fine particulate, and can be recovered in the Fines Screener 295 and recycled. Importantly, the Trichome Recycle material warms as it transfers through the process from the Trichome Pellet Mill and the Fines Screener, and serves to change the physical characteristics of the Trichome, making it much more suitable for pelleting in the Trichome Pellet Mill. The Trichome Recycle, being warmed from sub-zero temperatures to 0 degrees F. to 65 degrees F. (−17.8 degrees C. to 18.3 degrees C.), by the pelletizing and screening processes is more tacky and sticky than the incoming Lupulin from the Sifter 55, and will serve to increase cohesion as a sticking agent, when blended with the infeeding Trichome within the Trichome blend tank or Trichome Auger. It is conceived that the cool Trichome Recycle can aid significantly in pelleting the super cooled Trichome within the Trichome Pellet Mill.

Additionally, the Trichome Recycle 310 is a self-regulating feedstream, in that the colder the initial Trichome 206, fed into and processed by the Trichome Pellet Mill 285, the more Trichome remains un-pelleted, to pass through the Fines Screener and return to the Trichome Blend Tank 275, or returned to the Trichome Auger, in the Trichome Recycle stream, as discussed above. The Trichome Recycle in-turn, warms the stream of Trichome fed into the Trichome Pellet Mill as the Fine Fraction 258, thereby reducing the amount of un-pelleted Trichome passing through the Fines Screener, and so reduces the amount of Trichome Recycle.

As a significant benefit, the Trichome Recycle 310 serves to maintain product consistency, reduces process waste and because the Trichome Recycle automatically optimizes the temperature of the Trichome 206 feeding into the Trichome Pellet Mill 285, the Trichome Pellet Process 205 requires less oversight, less monitoring and reduces the need for fine control by process operators.

For the Trichome Pellet Product 300, the filling and packaging steps or processes are expected to be similar to the corresponding steps in the production of standard hop pellets, as is known to persons skilled in the technology of hop pellet processing. An automated apparatus for Bagging 315 is preferably employed as shown schematically in FIG. 4. Additionally, a Bagging Nitrogen 120 is injected into the packaged product, providing an inert atmosphere that is ideal for long term storage, displacing oxygen from the storage bag containing the Trichome Pellet Product.

In compliance with the statutes, the invention has been described in language more or less specific as to structural features and process steps. While this invention is susceptible to embodiment in different forms, the specification illustrates preferred embodiments of the invention with the understanding that the present disclosure is to be considered an exemplification of the principles of the invention, and the disclosure is not intended to limit the invention to the particular embodiments described. Those with ordinary skill in the art will appreciate that other embodiments and variations of the invention are possible, which employ the same inventive concepts as described above. Therefore, the invention is not to be limited except by the following claims, as appropriately interpreted in accordance with the doctrine of equivalents.

The following is claimed:

1. A trichome pelleting process comprising the steps of:
   a) feeding a bud cooled with a cryogenic fluid into a bud mill to separate the bud into component parts;
   b) sifting the bud to produce a fine fraction and a coarse fraction, the fine fraction including a trichome product, and the coarse fraction including a bract and calyx product;
   c) homogenizing and blending the fine fraction including the trichome product in a trichome blend tank;
   d) pelleting the fine fraction including the trichome product in a trichome pellet mill to produce a trichome pellet;
   e) cooling in the trichome pellet mill with a with a cryogenic fluid injected into a die of the trichome pellet mill;

f) screening the trichome pellet in a fines screener to produce a pellet fraction and an unders fraction, the pellet fraction comprising the a trichome pellet product and the unders fraction comprising a trichome recycle;

g) returning the trichome recycle to the trichome pellet mill;

h) feeding the trichome recycle to the trichome pellet mill the trichome recycle including the unders fraction comprising the trichome from the fines screener that fails to adhere into the trichome pellet, and with the trichome recycle remaining as a fine particulate and recovered in the fines screener, and the trichome recycle warming in the return of the trichome recycle to the trichome pellet mill from the fines screener as it feeds into the trichome pellet mill;

i) increasing cohesion of the trichome to the trichome pellet within the trichome pellet mill with an increase in a material transfer rate of the trichome recycle into the trichome pellet mill, the material transfer rate of the trichome recycle from the fines screener to the trichome pellet mill decreasing when the fine fraction including the trichome product warms in the trichome pellet mill to adhere to the trichome pellet and serve as a sticking agent within the trichome pellet; and j) decreasing sticking and clogging of the trichome within the trichome pellet mill with a decrease in the material transfer rate of the trichome recycle into the trichome pellet mill, the material transfer rate of the trichome recycle to the trichome pellet mill increasing when the fine fraction including the trichome product is too cold to adhere to the trichome pellet within the trichome pellet mill, and therefore the material transfer rate of the trichome recycle to the trichome pellet mill is self regulating in that the material transfer rate of the trichome recycle from the fines screener to the trichome pellet mill is dependent upon the trichome recovered in the fines screener as a function of the temperature within the trichome pellet mill.

2. The trichome pelleting process of claim 1, wherein the cryogenic fluid is a liquid nitrogen.

3. The trichome pelleting process of claim 1, additionally including the step of:

k) maintaining product consistency with the trichome recycle to reduce process waste with less oversight, less monitoring and to reduce oversight by a process operator by automatically optimizing the temperature of the trichome feeding into the trichome pellet mill.

4. The trichome pelleting process of claim 1, wherein the step of returning the trichome recycle to the trichome pellet mill additionally includes blending the trichome recycle with the fine fraction including the trichome product, and then feeding the trichome recycle with the fine fraction including the trichome product into the trichome pellet mill.

5. The trichome pelleting process of claim 1, wherein the step of returning the trichome recycle to the trichome pellet mill includes initially returning the trichome recycle to a trichome auger, to mix the trichome recycle with the fine fraction including the trichome product, and then feeding the trichome recycle with the fine fraction mixed with the trichome product into the trichome pellet mill.

6. The trichome pelleting process of claim 1, wherein the bud is a cannabis flower bud.

7. The trichome pelleting process of claim 6, wherein the step of sifting the bud to produce a fine fraction and a coarse fraction includes sifting the bud with a sieve having a mesh size above 0.14 mm with a substantial component portion of the bract and calyx material included in the fine portion.

8. The trichome pelleting process of claim 6, wherein the step of sifting the bud to produce a fine fraction and a coarse fraction includes sifting with a sieve having a mesh size between 0.14 mm and 1.0 mm with a substantial component portion of the bract and calyx material included in the fine portion.

9. The trichome pelleting process of claim 6, wherein the step of sifting the bud to produce a fine fraction and a coarse fraction includes selecting a sieve having a mesh size between approximately 0.07 mm and 0.14 mm.

* * * * *